(12) United States Patent
Ferrari

(10) Patent No.: US 7,691,047 B2
(45) Date of Patent: Apr. 6, 2010

(54) DEVICE FOR THE EPICARDIAL SUPPORT AND/OR RESUMPTION OF CARDIAC ACTIVITY

(75) Inventor: Markus Ferrari, Jena (DE)

(73) Assignee: PPA Technologies AG, Jena (DE)

( * ) Notice: Subject to any disclaimer, the term of this patent is extended or adjusted under 35 U.S.C. 154(b) by 464 days.

(21) Appl. No.: 11/569,036

(22) PCT Filed: May 10, 2005

(86) PCT No.: PCT/EP2005/005051

§ 371 (c)(1),
(2), (4) Date: Nov. 13, 2006

(87) PCT Pub. No.: WO2005/110512

PCT Pub. Date: Nov. 24, 2005

(65) Prior Publication Data

US 2007/0225545 A1    Sep. 27, 2007

(30) Foreign Application Priority Data

May 11, 2004    (DE) .................. 10 2004 023 190

(51) Int. Cl.
*A61H 31/00* (2006.01)
*A61M 1/10* (2006.01)

(52) U.S. Cl. .................................. 600/16; 623/3.1

(58) Field of Classification Search .............. 600/16, 600/17; 604/191; 606/191, 192; 623/3.1
See application file for complete search history.

(56) References Cited

U.S. PATENT DOCUMENTS

| 4,536,893 | A | * | 8/1985 | Parravicini | ............... 623/3.21 |
| 5,910,124 | A | * | 6/1999 | Rubin | ..................... 601/153 |
| 6,626,821 | B1 | * | 9/2003 | Kung et al. | ................. 600/16 |
| 6,699,259 | B2 | | 3/2004 | Fogarty et al. | |
| 2003/0088151 | A1 | | 5/2003 | Kung et al. | |
| 2004/0010180 | A1 | | 1/2004 | Scorvo | |
| 2004/0015043 | A1 | | 1/2004 | Frazier | |

FOREIGN PATENT DOCUMENTS

DE    19951220 A1    4/2001

* cited by examiner

*Primary Examiner*—Carl H Layno
*Assistant Examiner*—Gary A Porter, Jr.
(74) *Attorney, Agent, or Firm*—David S. Safran; Roberts Mlotkowski Safran & Cole, P.C.

(57) ABSTRACT

A device for epicardial support and/or the assuming of cardiac activity having a double membrane (1) consisting of an elastic inner membrane (2) and a non-expandable outer membrane (3) as well as a closed cavity (4) formed therebetween which can be inflated and deflated by means of a fluid. With the objective of further developing a device of the type as indicated at the outset which provides a simpler possibility of stimulating the heart in the critical post-operative phase, it is provided for at least one probe/electrode unit (7, 8) to be arranged on the inward facing side (6) of the inner membrane (2) to the heart (5) for epicardial ECG leads and/or signal transmission/conversion of an external pacemaker.

9 Claims, 4 Drawing Sheets

DEVICE FOR THE EPICARDIAL SUPPORT AND/OR RESUMPTION OF CARDIAC ACTIVITY

BACKGROUND OF THE INVENTION

1. Field of the Invention

The present invention relates to a device for epicardial support and/or the assuming of cardiac activity having a double membrane consisting of an elastic inner membrane and a non-expandable outer membrane as well as a closed cavity formed therebetween which can be inflated and deflated by means of a fluid.

2. Description of Related Art

Such a device—although one which works pericardially—is known for example from the document DE 199 51 220 A1. The device is a minimally-invasive, i.e. percutaneously implantable system for the mechanical support and temporary substitution of the heart's pumping function. After probing the pericardial sac, the device is inserted into the pericardial sac percutaneously in collapsed state or surgically positioned in the pericardial sac at the end of an operation with the double membrane surrounding the right and left ventricles. Thereby the device in its deflated state is so thin that a compression of the adjacent organs will be avoided. Subsequent implantation, the cavity of the double membrane is rhythmically supplied through a connecting tube with a fluid which can either be a gas (helium or $CO_2$) or a suitable liquid. Due to this rhythmic inflation and deflation of the double membrane's cavity and because the outer membrane is not expandable in contrast to the inner membrane, the double membrane surrounding the heart effects pressure transmission and compression of the heart. In so doing, blood is urged from the right ventricle into the pulmonary artery and simultaneously from the left ventricle into the aorta or, with available pumping function of the heart, aids in the systolic ejection of the cardiac muscle.

For patients who undergo heart surgery at the present time, however, a temporary pace-maker probe is still being attached epicardially at the end of the operation. In the case of asystolia (electrical cardiac standstill) or bradycardia (too slow of a heart rate) during the critical post-operative phase, the two temporary probes can stimulate the heart by means of an externally attached pacemaker. The probe cables are extracted after five to seven days, which is possible without reopening the chest. Yet regarded as a disadvantage is that those temporary pacemaker probe must every time be sewn on.

Should ventricular arrhythmias occur during the post-operative phase (ventricular tachycardia or ventricular fibrillation), a defibrillator must be used to restore the heart's normal rhythm. An external defibrillator attachable to the body is hereby used, although it is known on the one hand that only 10-20% of the energy in the form of electric work generated by the defibrillator (200 to 360 joules) acts directly on the heart, while most is absorbed by the surrounding tissue. On the other hand, implantable defibrillators can be used, whereby the probes positioned in the ventricle are usually left inside the patient for many years. Yet also known in this case is that usually only 30-50% of the energy generated by an implanted defibrillator (16 to 34 joules) has any effect on the heart.

SUMMARY OF THE INVENTION

Against the background of the disadvantages as described; i.e. the need to attach a temporary pacemaker probe and the large losses of energy when using known defibrillators, the object on which the present invention is based is that of further developing a device of the type as indicated at the outset which provides a simpler possibility of stimulating the heart in the critical post-operative phase.

This object is solved by a device for the epicardial support of cardiac activity of the type as indicated at the outset according to the invention which has at least one probe/electrode unit arranged on the inward heart-facing side of the inner membrane for epicardial ECG leads and/or signal transmission/conversion of an external pacemaker.

To be understood hereby by the term "probe" is a heart flow or cardiac pressure sensor and by the term "electrodes," electrical connecting members for the transmission of an electrical stimulus or pulse to the heart.

The advantages of the device according to the invention are in particular in that the epicardial ECG is obtained from probe/electrode unit(s) and is used for triggering, controlling the charge of the device in the pericardial sac and as a function control. The function control thereby includes the triggering of an alarm upon cardiac arrhythmia through to automatically activating the cardiac pacemaker, a defibrillating activity of the probe/electrode unit(s) respectively. Thus, with an externally-obtained ECG, the device represents an excellent alternative to conventional triggering. The epicardial sensors of the device according to the invention moreover self-transmit data on cardiac activity itself through the signals of the probe/electrode unit(s). The patient's recovery ("weaning") in the post-operative phase can thus be monitored, an indication of augmentation signaled, and the point in time to remove the device displayed. Furthermore, an automatic switching from "standby" (no supporting of the heart) to triggered augmentation (partial self-pumping of heart) all the way through to fully assuming cardiac activity (heart standstill) is, of course, possible.

Advantageous embodiments of the invention are specified below.

At least one probe/electrode unit is preferably allocated to each of the two ventricles, which also makes the device according to the invention applicable to bilateral heart failures.

In order to enable the probe/electrode unit(s) to be connected to devices external the patient, signal lines are preferably provided which are guided along the inward facing side of the inner membrane of the double membrane.

Pressure sensors are preferably arranged on the inner membrane to measure the systolic and diastolic blood pressure for allowing the device according to the invention for example with available pumping function of the heart, to be synchronizable with the heart action.

Also of advantage with respect to the pressure sensors is for the signal transmission of the pressure sensors to be to an external device via signal lines which are guided along on the inner side of the inner membrane.

The signal lines of the probe/electrode unit(s) and the pressure sensors preferably run into a common connector plug which can be connected to a corresponding terminal on an external control or drive unit.

It is provided for the double membrane to be collapsible and the probe/electrode unit(s) as well as the pressure sensors to be configured such that both their implantation as well as their explantation can ensue via percutaneous cannulation. Insofar there is no need to open the chest either during the operation nor post-operative.

Since external compression of the epicardial vessels is undesirable after coronary bypass surgery, the double membrane near the large coronary artery preferably comprises variable recesses. Such a double membrane can either be custom-made for a patient or, however, as a further advantageous embodiment provides, customized to the particular requirements of a patient's heart by means of displaceable supports. The variable recesses can thereby be brought into their desired position by the surgeon mechanically manipulating collapsible flexible bars or half-tubes. These collapsible flexible bars or half-tubes can be held in the desired position during pumping either by their own self-adhering properties, the use of a tissue adhesive, by a support rail or by grooves within the double membrane which force specific positions.

The following will make reference to a figure in describing an embodiment of the invention in greater detail.

DETAILED DESCRIPTION OF THE INVENTION

Figure 1:
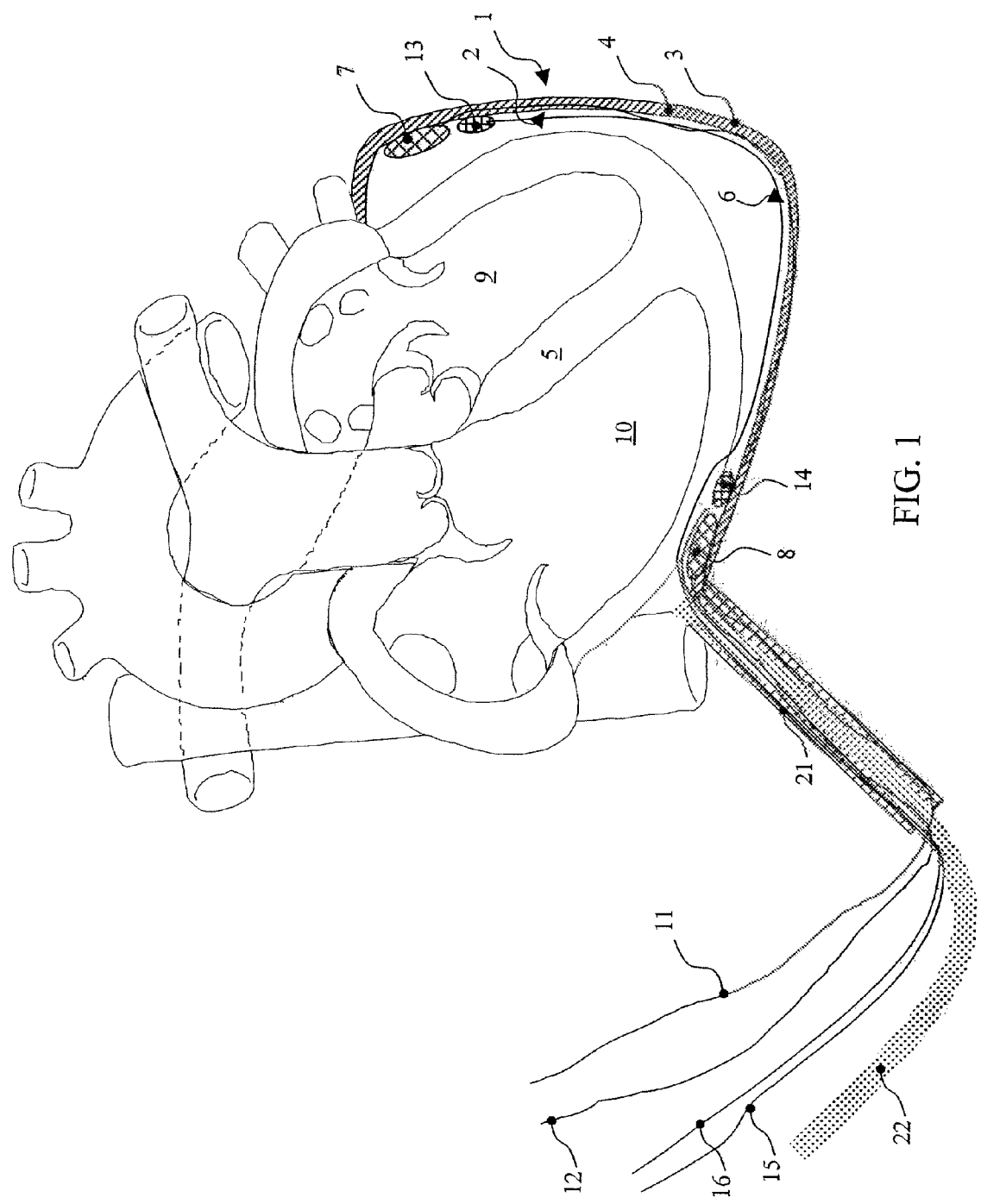
FIG. 1: a schematic representation of the device according to the invention.

FIG. 1 shows a schematic representation of a device for epicardial support and/or the assuming or resuming of cardiac activity having a double membrane 1 consisting of an elastic inner membrane 2 and a non-expandable outer membrane 3 as well as a closed cavity 4 formed therebetween which can be inflated and deflated by means of a fluid. Probe/electrode units 7, 8 are allocated to each ventricle 9, 10 at the inward facing side 6 of the inner membrane 2 to the heart 5 for the epicardial ECG lead and/or signal transmission/conversion for an external pacemaker. These probe/electrode units 7, 8 are connected to an external control or drive device which is not shown in this figure by means of signal lines 11, 12 guided along the inward facing side 6 of the inner membrane 2.

Pressure sensors 13, 14 are moreover arranged on the inward facing side 6 of the inner membrane 2 for measuring the systolic and diastolic blood pressure, which are likewise connected to the not shown external control unit by signal lines 15, 16 guided along the inward facing side 6 of inner membrane 2. In the implanted state, these signal lines 11, 12 and 15, 16 as well as a fluid tube 22 for inflating/deflating the cavity 4 run through an insertion catheter 21 in the skin beside the patient's sternum.

Figure 2:
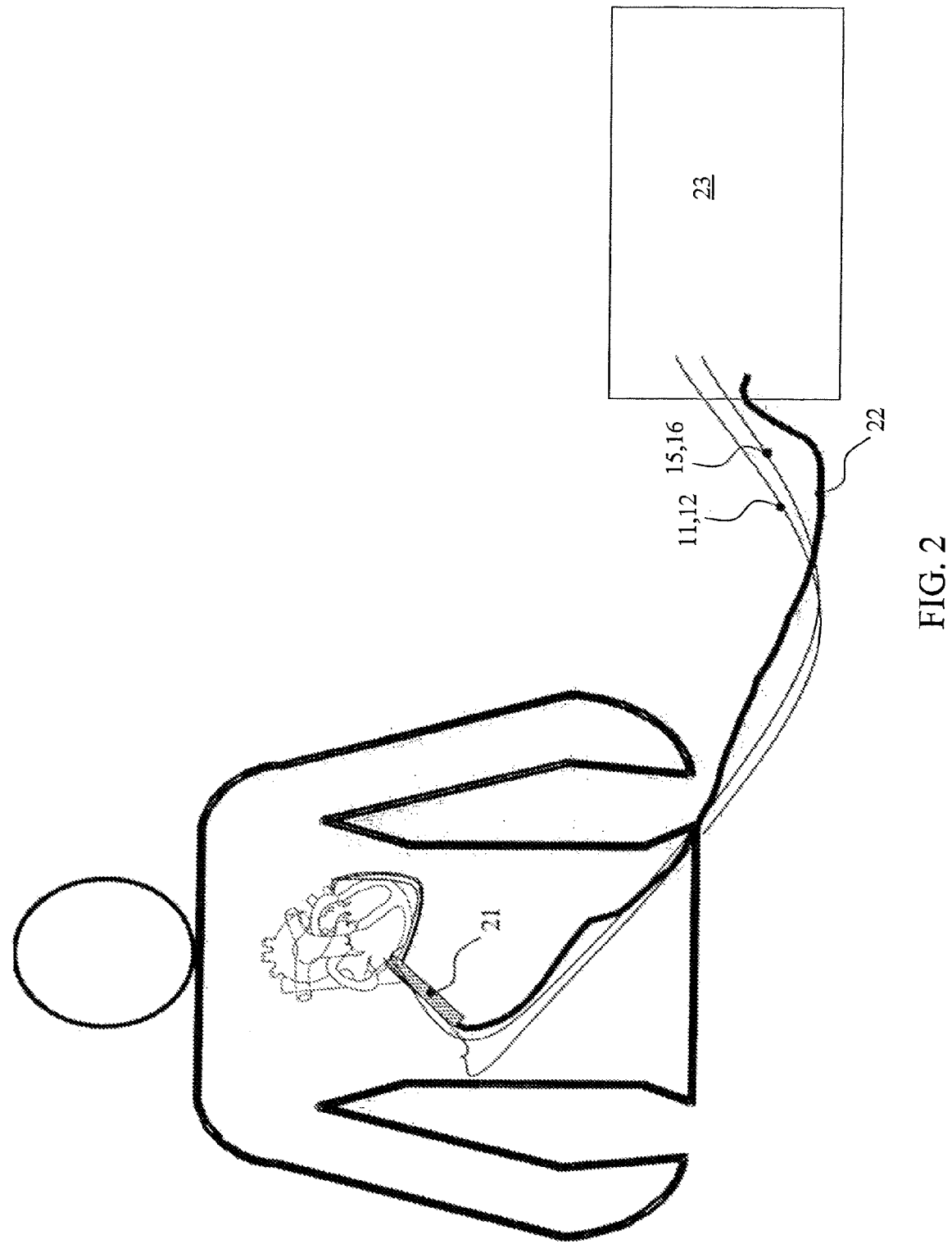
FIG. 2: a schematic representation of a patient with an implanted device according to the invention and an external control unit.

FIG. 2 shows a schematic representation of the location of an implanted double membrane 1 in a stylized patient torso as well as an external control and drive unit 23 supplied by the signal lines 11, 12 and 15, 16 and the fluid tube 22 by means of insertion catheter 21.

Figure 3:
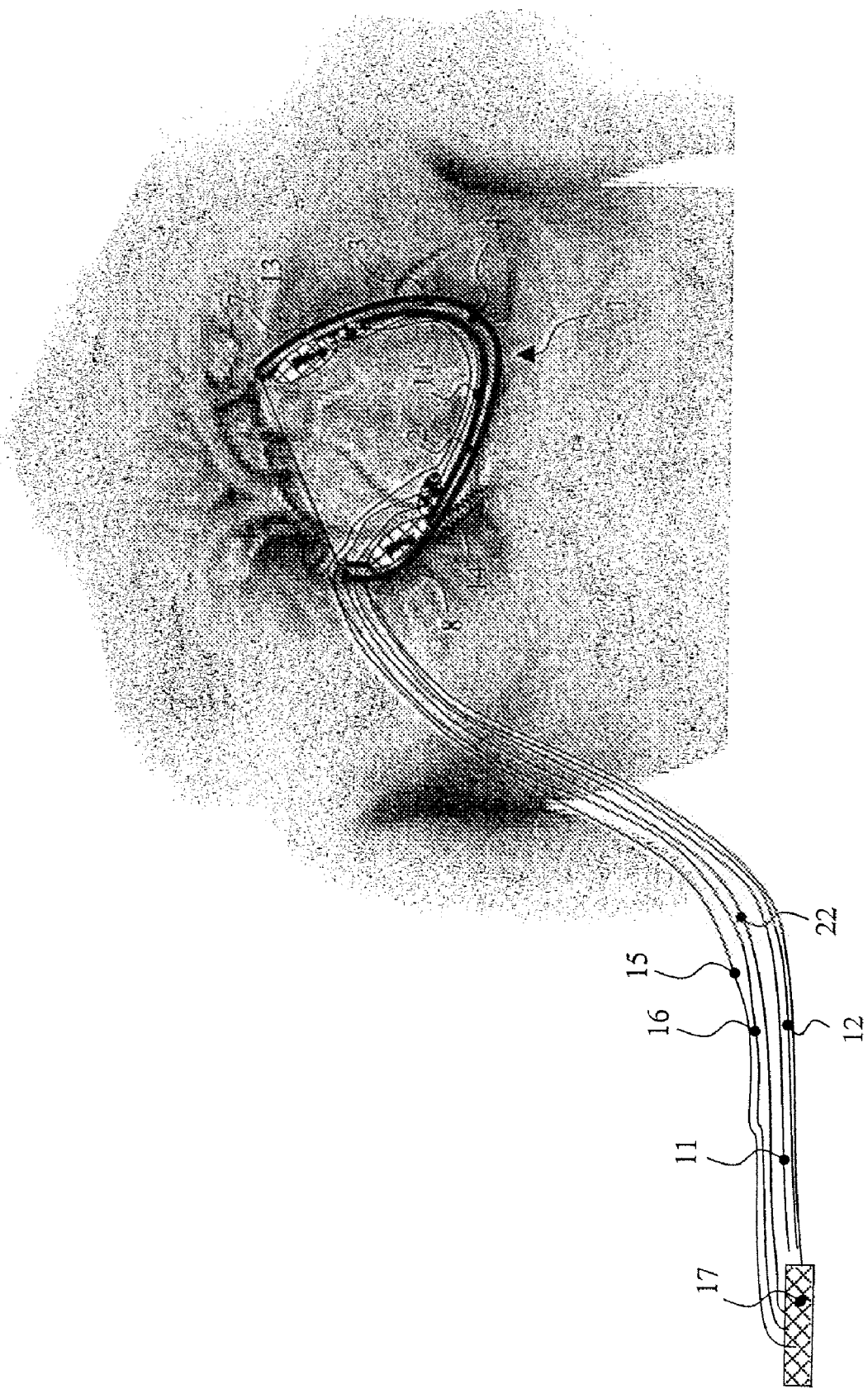
FIG. 3: a patient's opened chest with the implanted inventive device.

FIG. 3 shows the opened torso of a patient with a schematically-depicted double membrane 1 of the present invention projected thereon. The functional elements 7, 8 and 13, 14 as well as the cavity 4 are connected via fluid tube 22 (schematically depicted here by just a line) and via signal lines 11, 12 and 15, 16 to a common connector plug 17 by means of which the signal lines and the fluid tube can in turn be readily connected to the external control and drive unit 23 (not shown in this figure).

Figure 4:
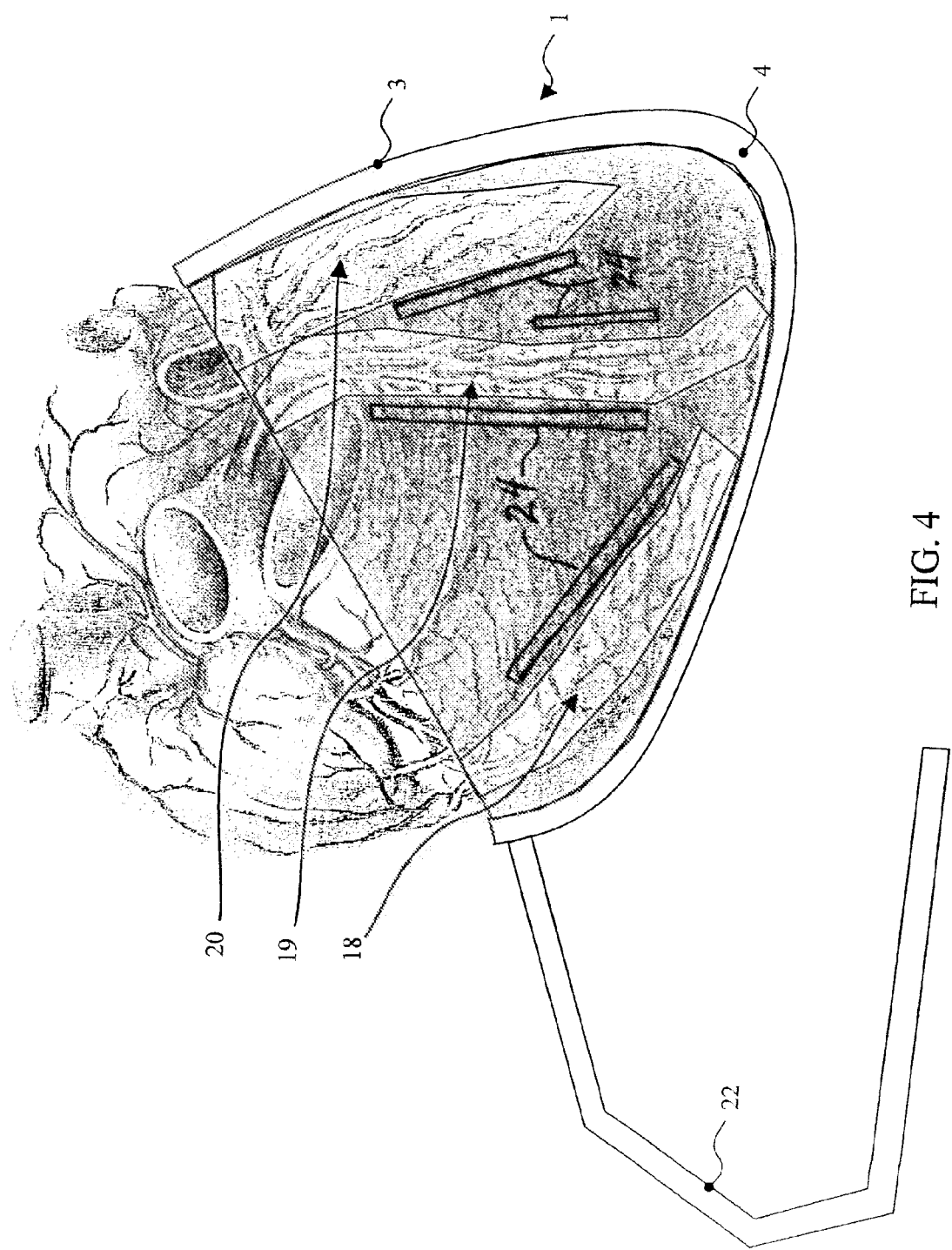
FIG. 4: a representation of the human heart with the inserted device and recesses.

FIG. 4 shows the heart of a patient with a schematically-depicted surrounding double membrane 1, the cavity 4 of which is in turn inflatable and deflatable by means of the fluid tube 22. This embodiment of double membrane 1 comprises variable recesses 18, 19, 20 in the area of the large coronary artery in order to avoid external compression of the epicardial vessels. These recesses 18, 19, 20 are customizable to the specific requirements of a patient's heart by means of displaceable supports which are not shown here.

What is claimed is:

1. A device for at least one of epicardial support and assuming of cardiac activity, comprising:
    a double membrane formed of an elastic inner membrane and a non-expandable outer membrane with a closed cavity being formed therebetween which can be inflated and deflated by means of a fluid;
    wherein at least one probe/electrode unit is arranged on an inward facing side of the inner membrane for at least one of epicardial ECG leads and signal transmission/conversion of an external pacemaker
    wherein variable recesses are provided in the double membrane in an area which, in use, is located in an area of the large coronary artery, the variable recesses being configured to be placed in their desired position between the membranes by displaceable supports confined within the closed cavity formed between the membranes.

2. The device according to claim 1, wherein at least one said probe/electrode unit is provided for allocation to each of two ventricles.

3. The device according to claim 1, wherein signal lines to the probe/electrode units are guided along the inward facing side of the inner membrane.

4. The device according to claim 1, wherein pressure sensors are arranged on the inner membrane to measure systolic and diastolic blood pressure.

5. The device according to claim 4, signal lines to the pressure sensors are guided along the inward facing side of the inner membrane.

6. The device according to claim 3, a common connector plug is provided for the signal lines.

7. The device according to claim 4, wherein the double membrane is collapsible and the probe/electrode units as well as the pressure sensors are configured for enabling implantation as well as their explantation thereof via percutaneous cannulation.

8. The device according to claim 1, wherein the displaceable supports comprise mechanically manipulatable collapsible flexible bars or half-tubes.

9. The device according to claim 8, wherein the collapsible flexible bars or half-tubes are fixable in the desired position by one of self-adhering properties of the flexible bars or half-tubes, a tissue adhesive, and a support rail or grooves within the double membrane.

* * * * *